United States Patent [19]

Sisti et al.

[11] Patent Number: 4,771,628

[45] Date of Patent: Sep. 20, 1988

[54] CHAMBER FOR CHROMATOGRAPHIC ANALYSES

[75] Inventors: Giorgio Sisti, Milan; Bruno Tosi, Carate Brianza; Giovanni Ostan; Fausto Munari, both of Milan; Ermete Riva, Merate, all of Italy; Sorin Trestianu, Brussels, Belgium

[73] Assignee: Carlo Erba Strumentazione, S.p.A., Milan, Italy

[21] Appl. No.: 465,265

[22] Filed: Feb. 9, 1983

[30] Foreign Application Priority Data

Feb. 17, 1982 [IT] Italy .................. 47818 A/82

[51] Int. Cl.⁴ .................................. G01N 30/02
[52] U.S. Cl. ............................ 73/23.1; 55/386
[58] Field of Search .......... 73/23.1; 55/386, 197, 55/267

[56] References Cited

U.S. PATENT DOCUMENTS

| 3,385,099 | 5/1968 | Diem et al. | 73/23.1 |
| 3,403,545 | 10/1968 | Carter | 73/23.1 |
| 4,070,169 | 1/1978 | Iwao et al. | 55/386 |
| 4,181,613 | 1/1980 | Welsh et al. | 73/23.1 |

FOREIGN PATENT DOCUMENTS 2054833A 2/1981 United Kingdom .

*Primary Examiner*—Stewart J. Levy
*Attorney, Agent, or Firm*—Millen & White

[57] ABSTRACT

This invention concerns a chamber for chromatographic analyses, in which capillary columns, in particular columns of fused silica, are thermally conditioned. The chamber comprises a thermally insulated space which can be perfectly sealed towards the outside and which houses means for heating the air and at least a fan for air circulation inside said space. In order to make the air flow going to the column(s) within the chamber as homogeneous and stable as possible from the thermal viewpoint the heating means are positioned on the suction side of the fan or of each fan, so to cause a perfect mixing of cold and hot fluid flow threads or lines in correspondence with the fan itself, and thereby obtain a uniform and stable air current from the fan towards the column.

9 Claims, 1 Drawing Sheet

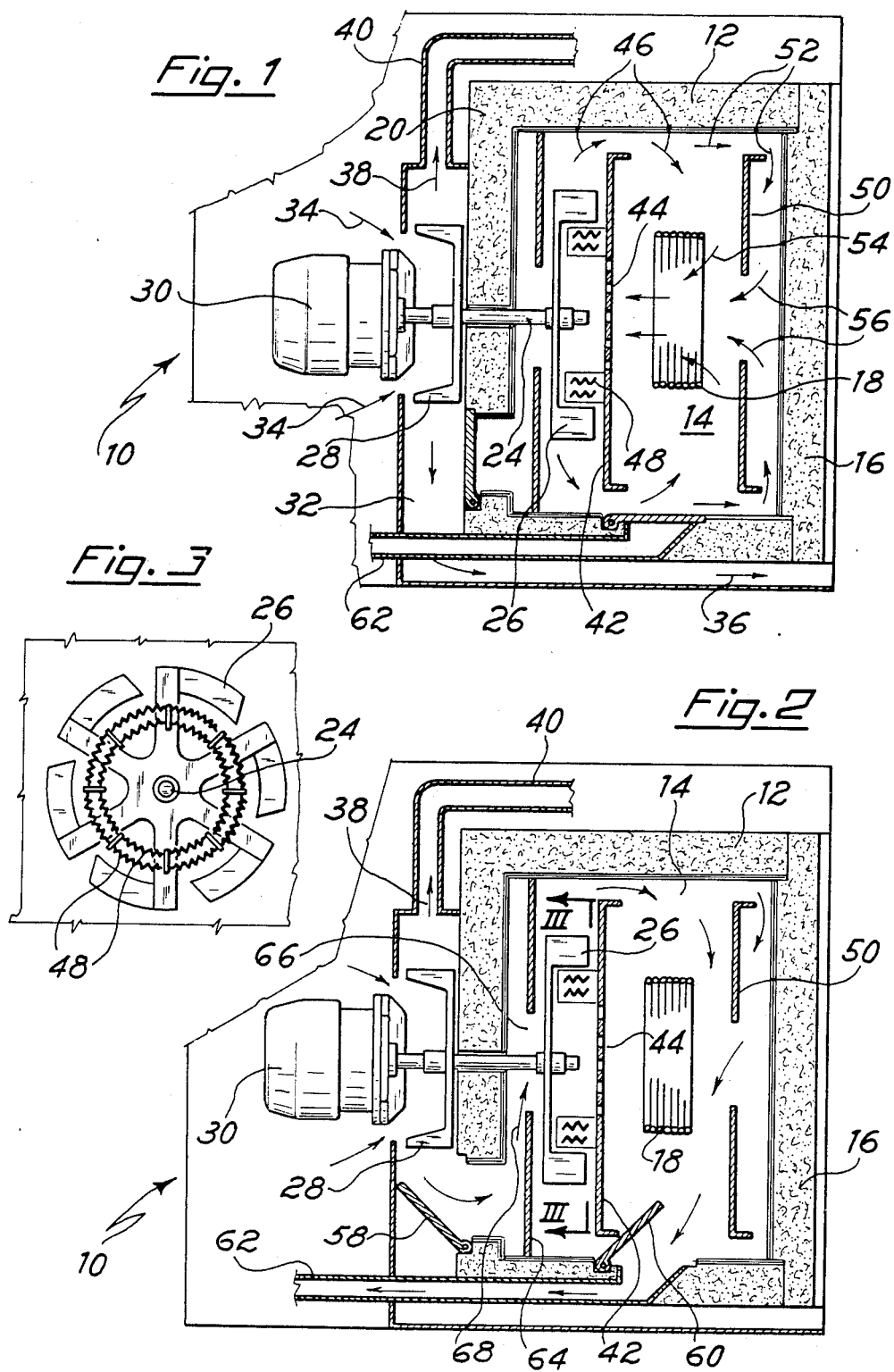

CHAMBER FOR CHROMATOGRAPHIC ANALYSES

BACKGROUND OF THE INVENTION

1. Field of the Invention

This invention concerns a chamber for chromatographic analysis, in which temperature conditions as necessary for the analytical use of packed or capillary chromatographic columns are obtained. The chamber is particularly suitable for use with thin-walled columns, such as fused silica columns. The chamber comprises in a known way, a thermally insulated space which can be sealed towards the outside, and housed within the space are means for air heating and at least a fan for air circulation inside the closed space.

2. DESCRIPTION OF THE PRIOR ART

Chambers of the above defined type are already known and used, in particular chambers in which the fan is of the type with axial or axial-radial suction and with radial delivery, and it is mounted near an inner wall of the chamber, behind a screen having a central opening to allow air to reach the fan, as well as with its edge spaced from the other internal walls of the chamber to create passage for the air flow, beyond the screen, towards the column. The heating means, generally consisting of electrical resistors, are positioned, in said known chambers, coaxially to the fan, with a suitable distribution, in general a uniform distribution, on the outside of the fan itself. In this way, a circulation inside the airtight space defined by the chamber is created, starting from the section area of the fan, in correspondence with the central opening of the screen, passing through the fan, where the fluid flow threads or lines are accelerated to be sent in contact with the electrical resistors, and finally reaching the the space occupied by the chromatographic column(s) beyond the edges of the screen.

This known solution has shown problems especially when using thin-wall capillary columns, such as fused silica columns, which have the inconvenience of an extremely reduced thermal inertia and therefore, a very high sensitivity to temperature changes, namely to quick local and time variations versus nominal values. In fact, it has been noticed that the analytical results sometimes are not correct (distorted or divided peaks) due to the fact that the temperature at any point of the column undergoes rapid changes in time versus its nominal temperature. This is due to an imperfect mixing of the flow threads or lines of cold and hot air, which contact the column in a casual way. The temperature variation at different points of the column produces, in the case of thin-walled capillary columns, an almost instant variation in the distribution of the components within the mobile and the stationary phase, in the mentioned points. As a result, a distortion of the peak occurs and such distortion, especially in the end section of the column, can no longer be eliminated or attenuated by the remaining stationary phase. The peak remains distorted or even divided until it enters the detector.

SUMMARY OF THE INVENTION

It is thus an object of the present invention to overcome this drawback by providing a chamber for chromatographic analyses in which the internal space, in particular during heating, when said space is sealed towards the outside, maintains the maximum temperature uniformity, and provides particular stability in correspondence with the area where the chromatographic column is positioned.

Another object of the present invention is to provide a new chamber for chromatographic analyses, of the above mentioned type, in which the temperature uniformity in space and stability in time in correspondence with the columns are not affected by the thermal inertia of the walls of the airtight space, and in particular by the temperature differences between the surface of said walls and the air which is circulated by the fan(s). According to the invention, these objects and other ones are achieved by providing a chamber for chromatographic analyses as previously defined, and essentially characterized in that the heating means thereof are positioned on the suction side of the fan or of each fan. In fact, it has been discovered that such positioning of the heating means permits creating, on the delivery side of the fan, a current of air having a substantially uniform temperature, thereby avoiding the creation of cold and hot flow threads or lines, at least in the portion which reaches the chromatographic column.

In the case where the fan is mounted behind a screen provided with a central opening for air inlet, as indicated above, the fan advantageously has a substantially cup-shaped configuration, open towards the screen, while electrical resistors are distributed coaxially to the fan, inside the cup configuration and are directly or indirectly supported by the screen. If the column is of the thin-walled type, it is advantageously supported inside the space defined by the chamber so as to be helicoidally wound in a coaxial way with respect to the fan and in such a way that the column has a winding diameter larger than or equal to the maximum size of the screen opening for air inlet. In this way, the air circulated by the fan passes beyond the edges of the screen and covers the entire space where the column is placed, hitting the latter, passing through it and then coming back in an axial direction towards the fan, which is reached after the air has passed through the zone of the resistors, wherein it is heated.

To avoid negative consequences on temperature stability due to the effect of the walls, it is advisable to place a second screen parallel to the former one, opposite to the column and presenting substantially the same configuration as the first screen, so that the fluid flow threads or lines contacting the walls of the closed space, and in this way undergoing cooling with respect to the main current which hits the column, are sent behind this second screen and again placed in circulation through the central opening of the latter, without thermally affecting the column.

BRIEF DESCRIPTION OF THE DRAWINGS

FIG. 1 is a schematic cross-sectional view of a chromatographic chamber according to the invention under heating conditions.

FIG. 2 is a schematic view, corresponding to that of FIG. 1, of the same chromatographic chamber under cooling conditions or conditions of temperature maintenance.

FIG. 3 is a schematic front view of the fan and of the heating resistors in the chamber of FIGS. 1 and 2, as seen in the direction of cross sectional line III—III of FIG. 2.

DETAILED DESCRIPTION OF THE PREFERRED EMBODIMENT

Referring to the drawings, the illustrated chamber comprises an external envelope 10 in which thermally insulating elements 12 are positioned which define in their inside a space 14 which can be sealed by means of a door 16, through which it is possible to reach said space for any operation to be performed on a capillary column 18, which is supported in a way known in itself in said space 14 and is helicoidally wound, as illustrated. Although it can be also used with other types of column, the chamber herein illustrated has been studied particularly for use with thin-walled columns, such as fused silica columns, having relatively a very reduced thermal inertia, and which are placed coaxially to the fans, as illustrated.

The insulated wall 20 opposite to the door 16 is crossed by a shaft 24 which bears a fan 26 mounted inside the space 14 which can be airtightly closed, as well as another fan 28 placed outside the space and the insulated walls, said shaft 24 being actuated, together with fans 26 and 28, by a motor 30. The external fan 28 works in a chamber 32 provided with openings to let air enter from the outside as indicated by arrows 34, said fan sending air 36 in until it reaches the internal surface of the envelope 10, in order to ensure that the latter does not reach temperatures which are dangerous to the operator who touches the equipment. Simultaneously, the fan 28 also sends air in 38 through a duct 40 which feeds other possible devices connected to the equipment, in particular, it performs the external cooling of a device for column direct injection.

The fan 26, mounted inside the closed space 14, is placed behind a screen 42 which extends perpendicular to the axis 24 of the fan and parallel to the insulated wall 20, and which presents a central opening 44, eventually protected by a grating, for axial inlet of the air which is circulated inside the space 14 by the fan 26. On the top side, the edges of screen 42 are spaced from the other walls of the space 14 to allow the air flow delivered by the fan 26 to pass beyond the screen 42, as indicated by arrows 46.

Behind the screen 42 and in the middle of fan 26, heating means are positioned, in the form of resistors 48 suitably distributed circumferentially with respect to the axis of fan 26. As shown in the drawing, the resistors 48 are placed on the suction side of fan 26. Therefore, the fluid flow threads or lines coming from opening 44 in axial direction are radially deviated and pass through the area of the resistors 48, heating themselves in a way that, considering the space distribution of said resistors 48, is not necessarily uniform. However, the subsequent passage through the blades of fan 26 makes the temperature of the fluid flow threads or lines completely uniform, creating a current which at all points has a constant temperature and which is sent behind the edges of the screen 42 until it reaches the walls of the column 18, then coming back to the opening 44 of screen 42; for instance through the central opening of the column 18. The diameter of the latter, when it is placed as in the Figures, is advantageously larger than or equal to the diameter or to the maximum size of the opening 44 of screen 42, so as to create a uniform circulation as above indicated.

In order to avoid that the fluid flow threads or lines, which belong to the air flow sent by the fan 26 and come in contact with the internal walls of the space 14 undergoing temperature variations, in particular cooling due to said contact, which negatively affect the performance of the chromatographic column 18, the invention proposes a second screen 50 placed in front of the first screen 42, in a position opposite to the column 18 and therefore in this case mounted on the door 16. This second screen 50 essentially shows the same configuration as the first screen, in a way that said fluid threads, undergoing temperature variations, are conveyed as indicated by arrows 52 towards the screen 50 and deviated by the latter to be then put again in circulation through the central opening 54 of the screen 50, as indicated by arrows 56. Considering the reciprocal position of the openings 54 and 44 in the screens and of the column 18 respectively, it can be clearly seen that these fluid threads, which follow arrows 52 and 56, are again circulated through the opening 44 in the screen 42, without touching the column 18 and therefore, without affecting the temperature conditions of the latter, in particular when it is positioned as in the Figure and when the diameter of the opening 54 is smaller than the winding diameter of the column.

To cool the space 14 where the column 18 is housed, air locks 58 and 60 respectively are foreseen, the first one of which communicates with the space 32 in which the external fan 28 works, while the air lock 60 opens on a duct 62 for air outlet towards outside. Moreover, between the wall 20 and the fan 26, there is a third screen 64 which separates the space 14 from the back wall 20, except for an opening 66 provided in said screen through which the air emitted by the fan 28 can be conveyed axially to the fan 26, as indicated by arrows 68, obviously when the air lock 58 is open. The air coming from outside and sent to the space 14 through the fan 28 is then distributed in said volume 14 by the fan 26 which then discharges said air flow through the air lock 60. To keep the termal conditions of the chamber at constant temperature values, it is also possible to choke the opening of air locks 58, 60, keeping resistors 48 connected. Also in this case it has been noticed that the uniformity of distribution and the stability of temperatures in correspondence with the column 18 are always satisfactory.

The above and further features of the invention may undergo to many differences and variations, without departing from the spirit and scope of the invention.

We claim:

1. A chamber for chromatographic analysis contructed for providing temperature conditions necessary to the analytical use of packed or capillary columns which are typically fused silica columns, said chamber defining a space sealable with respect to the exterior of said chamber, first fan means for circulating air housed in said chamber, said first fan means constructed for providing a suction fluid flow inwardly toward a center axis of rotation thereof, and then outwardly in a direction perpendicular to the center axis of rotation, and heating means positioned on the suction side of said first fan means for heating a fluid flow being drawn by suction into said first fan means center axis, when in operation, for heating thereof before being distributed by said first fan means whereby complete mixing of an already heated fluid flow being passed through said first fan means is ensured to provide a uniform temperature distribution in the fluid flow passed outwardly in the direction perpendicular to the center axis of rotation of said first fan means, at least one air lock means operable between a sealed position maintaining said chamber sealed with respect to the exterior, and an open position establishing communication between the exterior and the interior of the chamber, second fan means mounted coaxially to said first fan means, outside of said chamber, wherein at least one air lock means is positioned for receiving a fluid flow from said second fan means, and with flow directing means arranged inside the chamber for diverting a fluid flow from said second fan means into a flow which is in an axial direction to the first fan means for being distributed in the chamber thereby, and said flow diverting comprising a second fluid screen with an opening in the center thereof, and said screen extending parallel to and spaced between said first, whereby the fluid flow from the exterior can be passed to said first fan means for distribution therefrom through said screen opening.

2. A chamber for chromatographic analysis constructed for providing temperature conditions necessary to the analytical use of packed or capillary columns including thin-wall capillary columns which are typically fused silica columns, said chamber defining a space sealable with respect to the exterior of said chamber, first fan means for circulating air housed in said chamber, said first fan means constructed for providing a suction fluid flow inwardly toward a center axis of rotation thereof, and then outwardly in a direction perpendicular to the center axis of rotation, said first fan means comprising a fan constructed for providing suction in at least its axial direction and delivery in its radial direction, said fan being mounted adjacent a first internal wall of said chamber and behind a first screen having at least one central opening, said first screen positioned on the suction side of said fan to provide for a fluid flow through said at least one central opening to said fan, said fan having a substantially cup-shaped configuration open towards said first screen, heating means positioned on the suction side of said fan for heating a fluid flow being drawn by suction into said fan through the center axis thereof before contacting said fan, when in operation, said heating means comprising eletrical resistors supported directly or indirectly by said first screen in a distribution co-axial to the fan inside the cup-shaped configuration thereof, and on the suction side of the fan for heating the fluid flow being drawn in before being distributed by the blades of the fan whereby complete mixing of an already heated fluid flow being passed through the fan is ensured to provide uniform temperature distribution in the fluid flow passed outwardly in the direction perpendicular to the center axis of rotation of the fan, and a second screen positioned parallel to said first screen on the other side of a column arranged in the chamber with respect to said first screen, said second screen having its edges spaced from the internal walls of the chamber for defining passages for fluid flow therethrough, and said second screen having a central opening aligned with the central opening of said first screen for having fluid flow passing through said defined passages between said second screen and the internal walls of the chamber pass through said second screen second opening into contact with a column in the screen in a direction toward the central opening of said first screen.

3. A chamber as in claim 2 wherein a helicoid wound thin walled column is arranged in said chamber on a side of said first screen opposite to said fan and coaxially positioned with respect to said fan with the winding size of said column being greater than the central opening in the first screen, and said first screen being positioned parallel to the first internal wall of the chamber and having edges spaced from the internal walls of the chamber adjacent the edges thereof for defining passages for fluid flow from the fan to the column, and wherein the size of the central opening of the second screen is smaller than the winding diameter of the column.

4. A chamber for chromatographic analysis constructed for providing temperature conditions necessary to the analytical use of packed or capillary columns including thin-wall capillary columns which are typically fused silica columns, said chamber defining a space sealable with respect to the exterior of said chamber, first fan means for circulating air housed in said chamber, said first fan means contructed for providing a suction fluid flow inwardly toward a center axis of rotation thereof, and then outwardly in a direction perpendicular to the center axis of rotation, said first fan means comprising a fan constructed for providing suction in at least its axial direction and delivery in its radial direction, said fan being mounted adjacent a first internal wall of said chamber and behind a first screen having at least one central opening, said first screen positioned on the suction side of said fan to provide for a fluid flow though said at least one central opening to said fan, said fan having a substantially cup-shaped configuration open towards said first screen, and heating means positioned on the suction side of said fan for heating a fluid flow being drawn by suction into said fan through the center axis thereof before contacting said fan, when in operation, said heating means comprising electrical resistors supported directly or indirectly by the first screen in a distribution co-axial to the fan inside the cup-shaped configuration thereof, and on the suction side of the fan for heating the fluid flow being drawn in before being distributed by the blades of the fan whereby complete mixing of an already heated fluid flow being passed through the fan is ensured to provide uniform temperature distribution in the fluid flow passed outwardly in the direction perpendicular to the center of axis of rotation of the fan.

5. A chamber as in claim 4 wherein a helicoid wound thin walled fused silica capillary column is arranged in said chamber on a side of said first screen opposite to said fan with the winding size of said column being greater than the central opening in the first screen, and said first screen being positioned parallel to the first internal wall of the chamber and having edges spaced from the internal walls of the chamber adjacent the edges thereof for defining passages for fluid flow from the fan to the column.

6. A chamber as in claim 4 further comprising at least one air lock means operable between a sealed position maintaining said chamber sealed with respect to the exterior, and an open position establishing communication between the exterior and the interior of the chamber.

7. A chamber as in claim 6 further comprising second fan means mounted coaxially to said first fan means, outside of said chamber, wherein at least one air lock means is positioned for receiving a fluid flow from said second fan means, and with flow diverting means arranged inside the chamber for diverting a fluid flow from said second fan means into a flow which is in an axial direction to the first fan means for being distributed in the chamber thereby.

8. A chamber as in claim 4 wherein the chamber is defined by insulated walls.

9. A chamber as in claim 4 wherein said at least one opening of the first screen is covered by a grating.

* * * * *